United States Patent
Lu et al.

(10) Patent No.: US 6,696,478 B2
(45) Date of Patent: Feb. 24, 2004

(54) CANCER TREATMENT WITH GÖ6976 AND ITS RELATED COMPOUNDS

(76) Inventors: Zhimin Lu, 8452 New Salem St., #20, San Diego, CA (US) 92126; Keming Wang, 79 East Ximei Street, Apt. 303, Suzhou (CN), 215002

( * ) Notice: Subject to any disclaimer, the term of this patent is extended or adjusted under 35 U.S.C. 154(b) by 0 days.

(21) Appl. No.: 09/912,758

(22) Filed: Jul. 24, 2001

(65) Prior Publication Data

US 2002/0016352 A1 Feb. 7, 2002

Related U.S. Application Data

(63) Continuation-in-part of application No. 09/370,190, filed on Aug. 9, 1999.

(51) Int. Cl.$^7$ ................................................. A61K 31/40
(52) U.S. Cl. ...................................................... 514/410
(58) Field of Search .......................................... 514/410

(56) References Cited

U.S. PATENT DOCUMENTS 6,407,058 B1 * 6/2002 Staddon et al. ............. 514/414

* cited by examiner

*Primary Examiner*—Jerome D. Goldberg
(74) *Attorney, Agent, or Firm*—John R. Ross; John R. Ross, III

(57) ABSTRACT

A chemotheraputic cancer treatment in which Gö6976 or a compound chemically similar to Gö6976 is administered to a mammal for the treatment of the cancer. The chemical compound is targeted to PKC α activity. Experiments have shown Gö6976 and similar compounds to be effective for the treatment of breast cancer, leukemia, lung cancer, bone cancer, skin cancer, prostate cancer, liver cancer, brain tumor, cervical cancer, and cancers located in the digestive tract including gastric cancer and colorectal cancers. These treatments may be accomplished utilizing Gö6976 and compounds similar to it alone or in combination with prior art chemotherapy agents or with radiation therapy. In a preferred embodiment Gö6976 is used for the treatment of cancer as a preventative drug by preventing cancer cell formation.

31 Claims, 8 Drawing Sheets

PRIOR ART

Gö6976

C-o 002

C-o 003

CANCER TREATMENT WITH GÖ6976 AND ITS RELATED COMPOUNDS

This application is a continuation-in-part application of Ser. No. 09/370,190 filed Aug. 9, 1999. This invention relates to cancer treatments and especially to cancer treatments directed to protein kinase C α enzyme.

BACKGROUND OF THE INVENTION

Researchers have recognized that a family of enzymes known as protein kinase C enzymes is associated with a large number of cancers. This family includes at least eleven isoenzymes. A particular member of this family is identified as the protein kinase C alpha enzyme, abbreviated: PKC α.

Researches have reported increases in PKC α activity in human breast tumors (NG et al., Science. 283:2085–2089) and significant increases in PKC α expression in prostate cancers (Cornford et al., Am. J. Pathol. 154: 137–144). Researchers have reported that PKC α is required for the metastasis of human melanoma (Dennis et al., Cancer Lett. 128:65–70) and that PKC α is related to the progression of brain tumors (Shen et al., Mol. Pharmacol. 55:396–402). Recently, Muller et al were granted a patent, U.S. Pat. No. 5,744,460, which discloses a cancer treatment utilizing an antisense oligonuclotide targeted to PKC α combined with a chemotherapeutic agent. U.S. Pat. Nos. 5,882,927 and 5,885,970 issued to Bennett et al also disclose antisense oligonuclotides targeted to PKC.

A chemical known as Gö6976, available from Calbiochem Corp. and Alexis Corp. (both with offices in San Diego, Calif.), is known to be an inhibitor of PKC α. Gö6976 is designated as C24H18N40 and a diagram of the molecule is presented in FIG. 1. Applicant et al reported in Molecular Cellular Biology, 17:3418–3428 based on a variety of experiments that Gö6976 prevented TPA-induced downregulation of the of PKC α and is a more specific inhibitor for PKC α. What is needed is a better treatment for cancer.

SUMMARY OF THE INVENTION

The present invention provides a chemotheraputic cancer treatment in which Gö6976 or a compound chemically similar to Gö6976 is administered to a mammal for the treatment of the cancer. The chemical compound is targeted to PKC α activity. Experiments have shown Gö6976 and similar compounds to be effective for the treatment of breast cancer, leukemia, lung cancer, bone cancer, skin cancer, prostate cancer, liver cancer, brain tumor, cervical cancer, and cancers located in the digestive tract including gastric cancer and colorectal cancers. These treatments may be accomplished utilizing Gö6976 and compounds similar to it alone or in combination with prior art chemotherapy agents or with radiation therapy. In a preferred embodiment Gö6976 is used for the treatment of cancer as a preventative drug by preventing cancer cell formation. In a preferred embodiment the chemical targeted to PKC α is a chemical having the following structure:

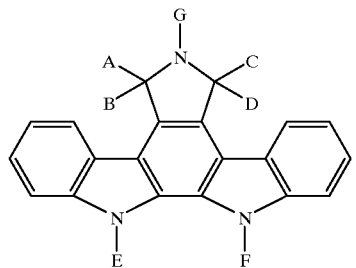

where A, B, C, D, B, F and G are each a modifying chemical or chemical compound.

The modifying chemical or chemical compound may consists of a chemical or chemical compound of the following group of chemicals and chemical compounds: hydrogen, an oxygen, methyl, ethyl, propyl, or isopropyl, carboxymethyl, 2-carboxyethyl, or 3-carboxypropyl, a straight or branched alky of from 1 to a number of carbon atoms, a straight or branched azidoalkyll, carboxyalkyl, amidinothioalkyl, amidinoalkyl, (2-nitroguanidino) alkyl, containing in each case from 1 to a number o carbon atoms, or—(CH2) 2-CO—NX wherein X can be each independently hydrogen, alkyl of from 1 to a number of carbon atoms or benzyl. Preferred chemicals for use in accordance with the present invention are:

A) Gö6976 (trade name): $C_{24}H_{18}N_4O$ (formula): 12-(2-Cyanoethyl)-6,7,12,13-tetrahydro- 13-methyl-5-oxo-5H-indolo[2,3-a]pyrrolo[3,4-c]carbazole (chemical name), B) C-o 002 (trade name): $C_{23}H_{22}N_4$ (formula): 12-(3-Aminopropyl)-5,6,7,12,13-pentahydro-indolo[2,3,-a] pyrrolo [3,4-c] carbazole (chemical name)

C) C-o 003 (trade name): $C_{23}H_{24}N_4Cl_2$ (formula): 12-(3-Aminopropyl)-5,6,7,12,13-pentahydro-indolo[2,3,-a] pyrrolo [3,4-c] carbazole hydrochloride (chemical name).

DETAILED DESCRIPTION OF PREFERRED EMBODIMENTS

The present invention may be described by reference to the figures. Several varieties of cancer cells were grown in laboratory conditions and tested with Gö6976 and the results recorded. The experiments and the results are described below.

First Set of Experiments

A first set of experiments were conducted as described below:
Cell Culture
Cell cultures used the following cancer cells, which were supplied from the American Type Culture Collection, Rockville, Md.:

MDA-MB-468 human breast cancer cells,
MDA-MB-453 human breast cancer cells,
A431 human epidermoid carcinoma cells,
U-2 OS human osteosacoma cells,
3Y1 rat fibroblast cells overexpressing the epidermal growth factor receptor (EGFR).

These cells were maintained in Dulbecco's modified Eagle medium (DMEM) supplemented with 10 percent bovine calf serum.

Small cell lung cancer cells (NCI-H048),
Non-small cell lung cancer cells (NCI-H2342).

Small cell lung cancer cells were grown in RPMI 1640 medium with 2 mM L-glutamine adjusted to contain 1.5 g/L sodium bicarbonate, 4.5 g/L glucose, 10 mM HEPES, 1.0 mM sodium pyruvate, and 5% fetal bovine serum. Non-small cell lung cancer cells were grown in RPMI 1640 medium supplemented with 5% fetal bovine serum, 5 ug/ml insulin, 10 ug/ml transferrin, 30 nM sodium selenite, 10 nM hydrocortisone, 10 nM beta-estradiol, 10 mM HEPES, and 2 mM L- glutamine.

HL60 human acute promyelocytic leukemia cells were grown in RPMI 1640 medium containing 10 percent heat-inactivated fetal bovine serum (FBS).

For growth of these cells in soft agar, $1 \times 10^3$ cells were suspended in top agar (consisting of 20 percent calf serum, 0.38 percent agar and the remainder DMEM) and overlaid onto hardened bottom agar (DMEM, 20 percent calf serum and 0.7 percent agar) as reported by Sementchenko et al, in Onocgen 17:2883–2888.

Materials

Gö6976 was obtained from Calbiochem.

Cell Viability Assay

Cells were seeded for 24 hours. Then they were either treated with Gö6976 or left untreated. The cells were then collected periodically and evaluated using trypan blue dye exclusion to asses viability using the method described by CY Chen, et al, in J.Biol. Chem. 273:16700–16709.

Experimental Results

Breast Cancer

Figure 1:
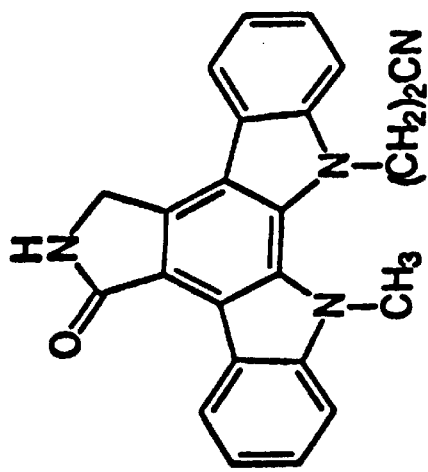
FIG. 1 is chart showing the chemical structure of Gö6976.
Figure 2:
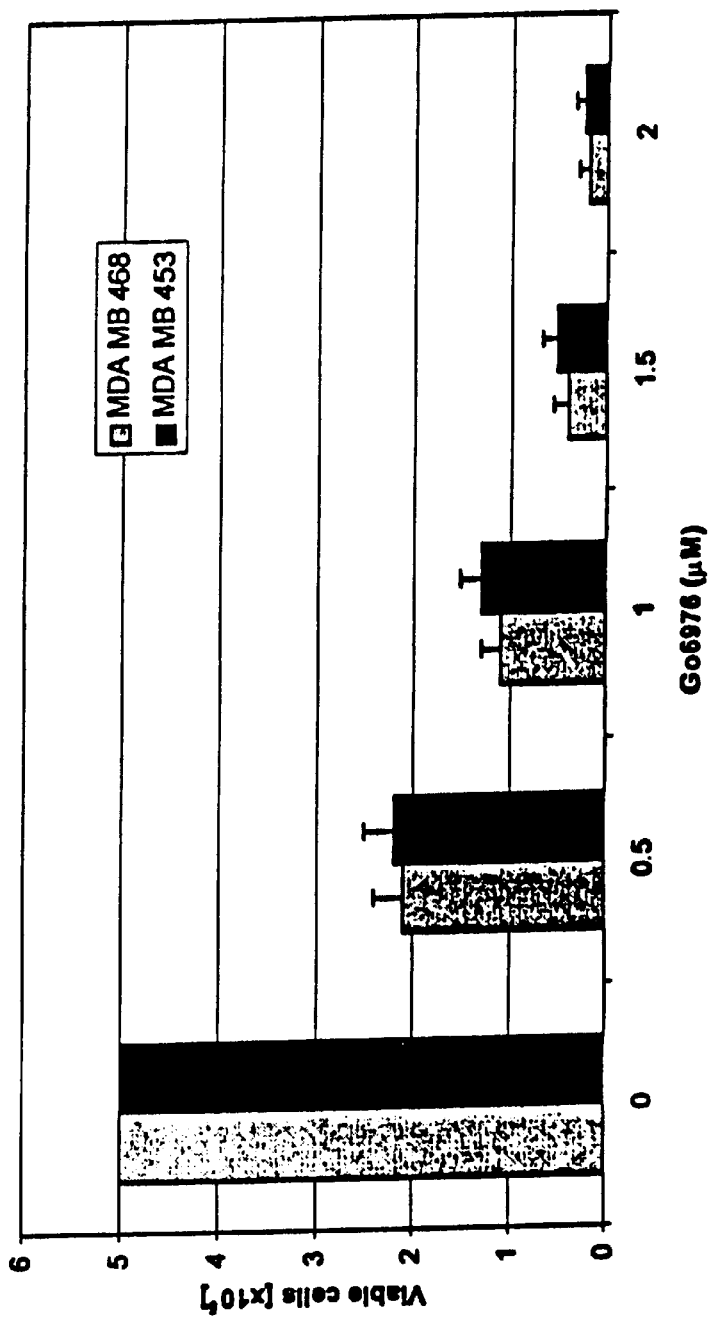
FIGS. 2 through 8 are graphs showing the results of treating various cancer cells with Gö66976.
Figure 3:
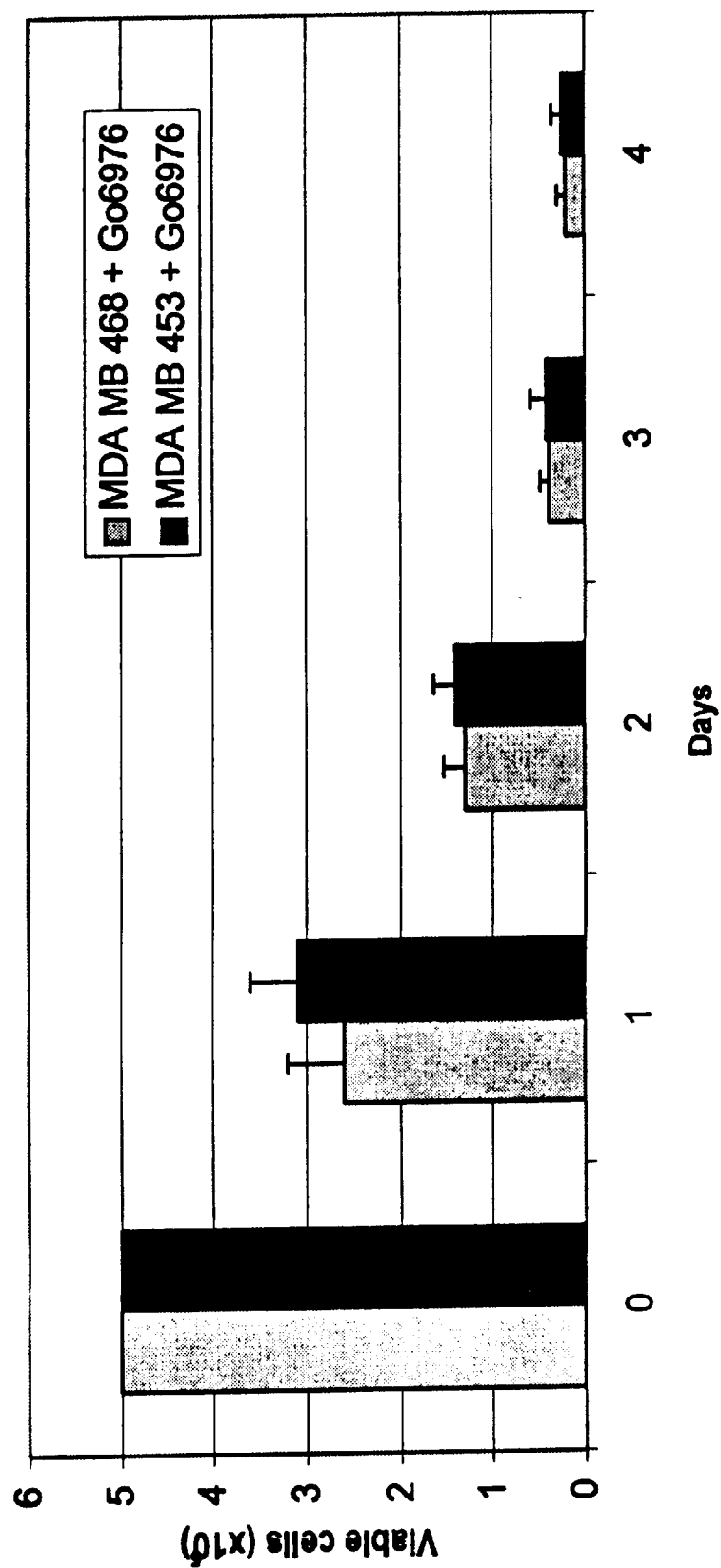

The results of treatment of human breast cancer cells (MDA-MB-468 and MDA-MB-453 with Gö66976 are shown in FIGS. 2 and 3. Cultures containing about $5 \times 10^5$ cells were treated with 0.0, 0.5, 1.0 and 2.0 micromole of Gö6976 and the viable cells were counted at day 4. As shown in FIG. 2 cell count was reduced to about $1 \times 10^5$ when treated with 1 micromole of Gö6976 and to less than $0.3 \times 10^5$ when treated with 2.0 micromolar of Gö66976. In a separate experiment as shown in FIG. 3, the breast cancer cells were treated with 2.0 micromoles of Gö6976 and measurements made at 24 hours intervals for 4 days. Viable cell concentration appears to be reduced by approximately half each 24 hours. In both FIG. 2 and FIG. 3 error bars indicated the estimated standard error based on three independent experiments.

Leukemia

Figure 4:
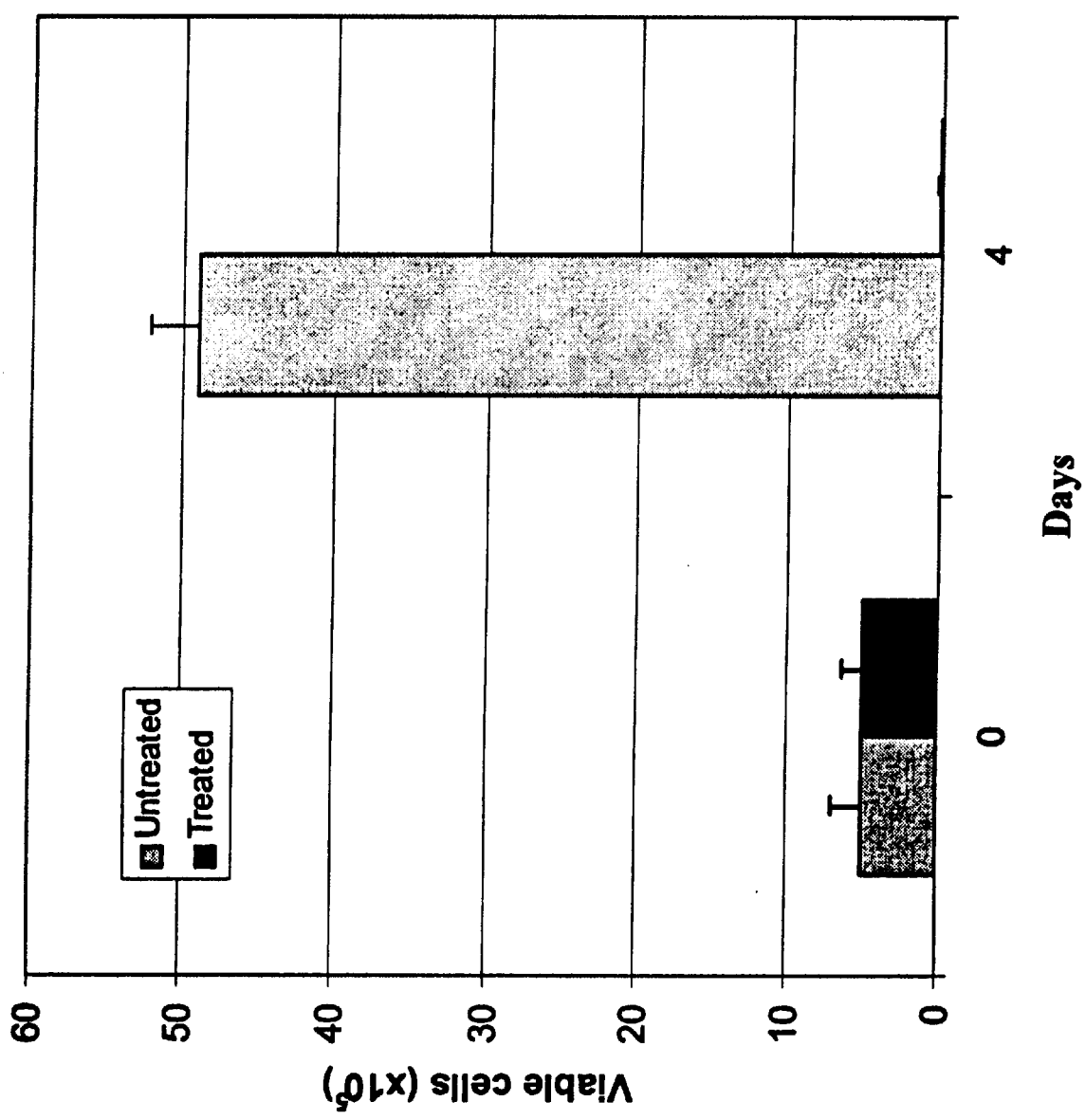

The results of treatment of HL60 acute promyelocytic leukemia cells with Gö6976 are shown in FIG. 4. One of two samples of $5 \times 10^5$ cells was treated with 2 micromoles of Gö6976 and the viable cells were counted after four days. At four days the cells in the untreated sample had grown by a factor of nearly 10 to almost $5 \times 10^6$ cells whereas viable cells in the treated sample was less than $0.2 \times 10^5$.

Lung Cancer

Figure 5:
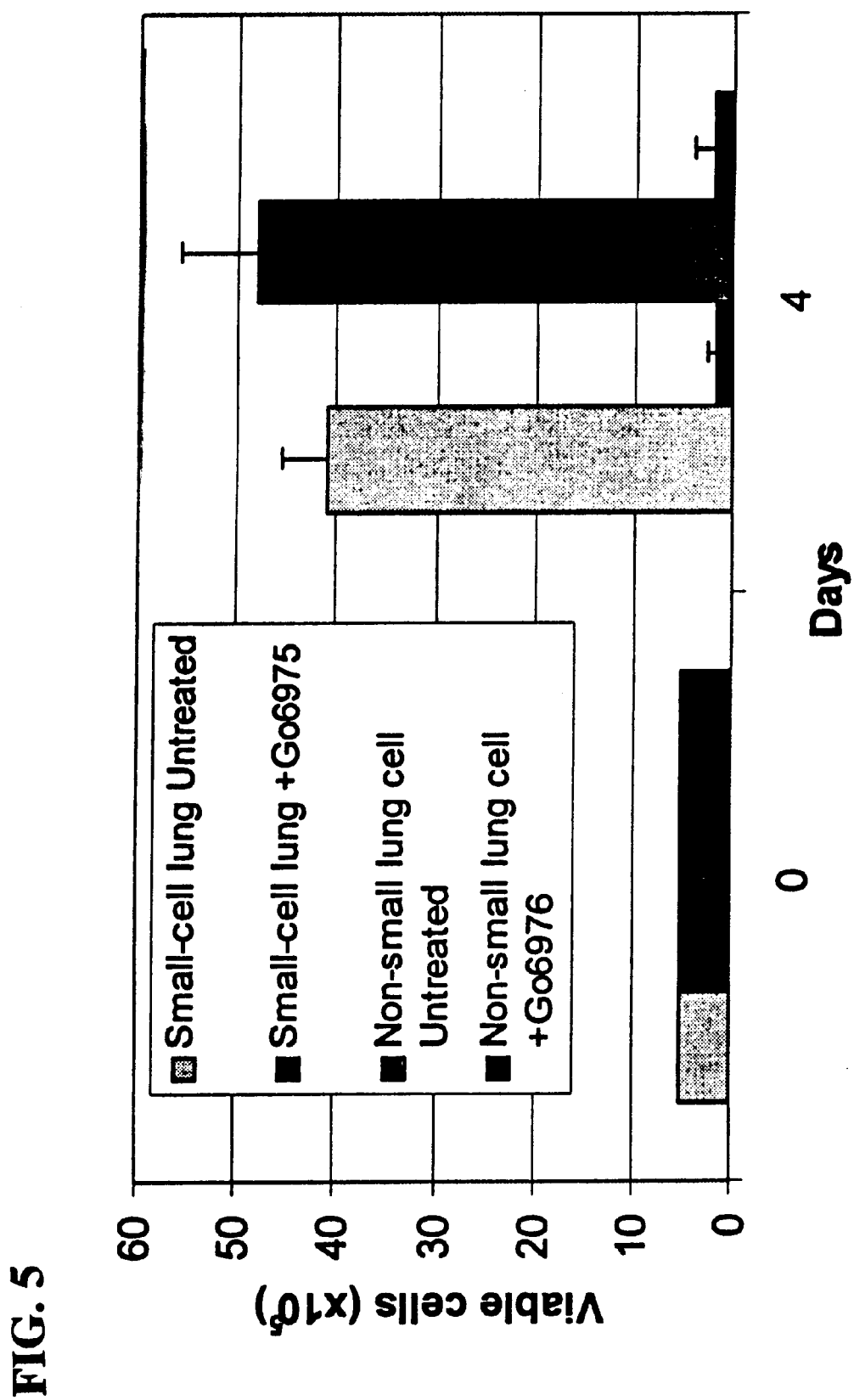

The results of treatment of lung cancer cells are shown in FIG. 5. Two samples each of about $5 \times 10^5$ cells small lung cancer cells and non-small lung cancer cells were prepared and one sample of each type was treated with Gö6976 and the viable cells were counted at day 4. In the untreated samples the cancer cells had multiplied by almost a factor of 10 and in the treated samples the count had decreased to less than 0.5 of the original count.

Bone Cancer

Figure 6:
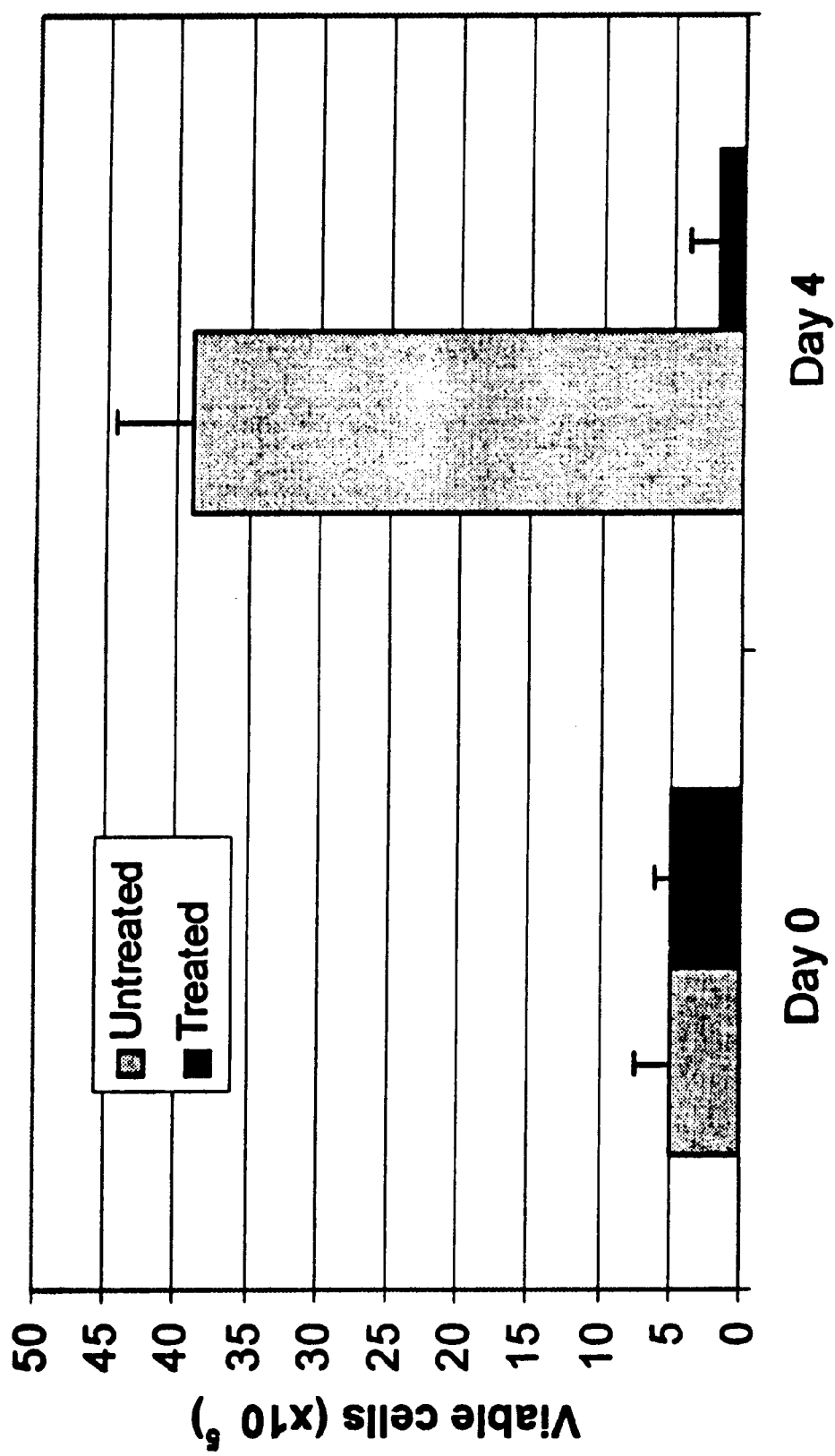

The results of treatment of osteosarcoma cells are shown in FIG. 6. One of two samples of about $5 \times 10^5$ cells was treated with 2 micromoles of Gö6976 and the viable cells were counted after four days. At four days the cells in the untreated sample had grown by a factor of nearly 8 to almost $4 \times 10^6$ cells whereas viable cells in the treated sample were reduced to about half the original count.

Skin Cancer

Figure 7:
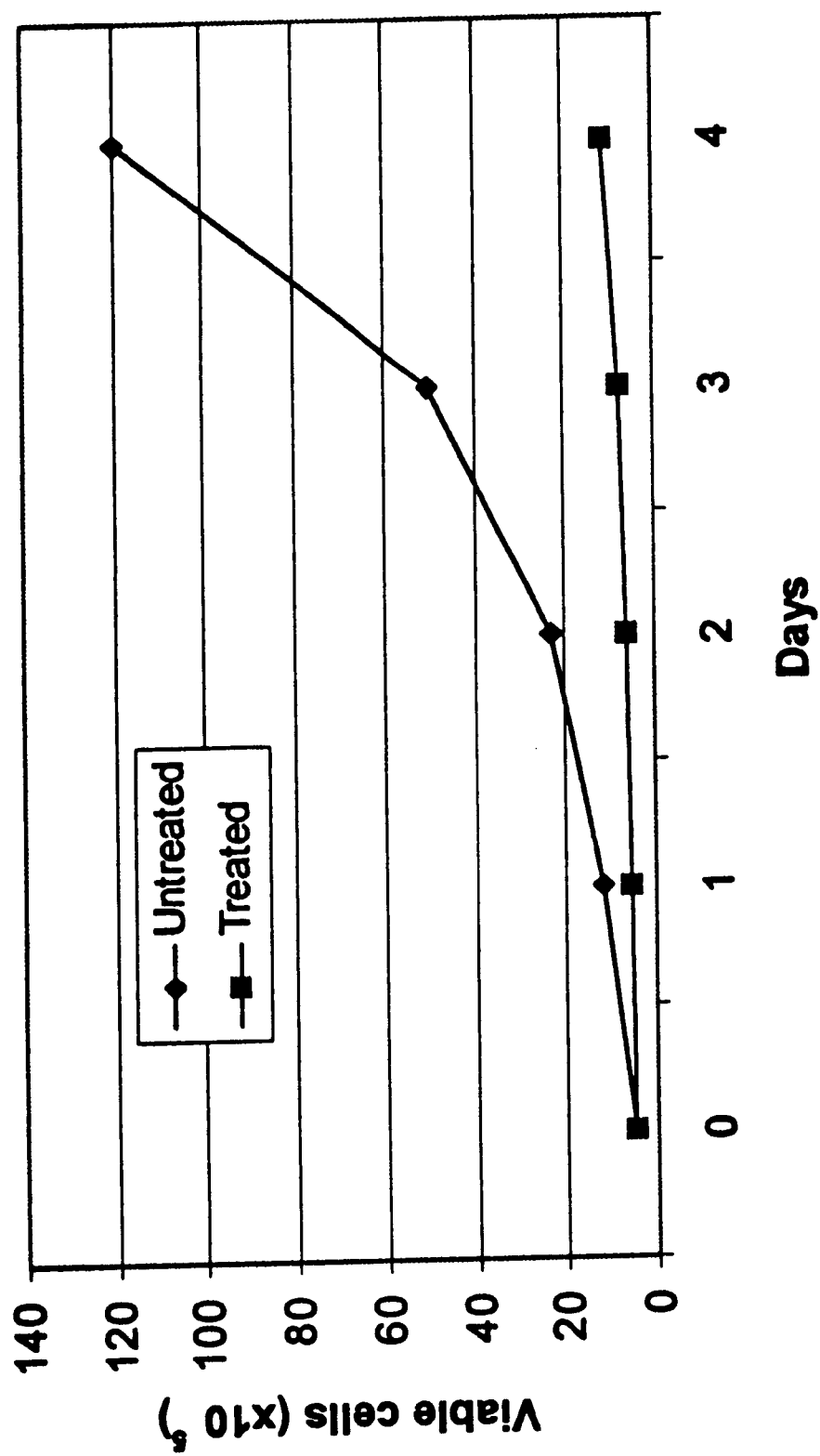

The results of treatment of A431 human epidermoid carcinoma cells are shown in FIG. 7. One of two samples of about $5 \times 10^5$ cells was treated with 2 micromoles of Gö6976 and the viable cells were counted each 24 hours for four days. At four days the cells in the untreated sample had grown by a factor of about 24 to almost $1.2 \times 10^7$ cells whereas viable cells in the treated sample had approximately doubled.

EGF Induced Cell Transformation

Figure 8:
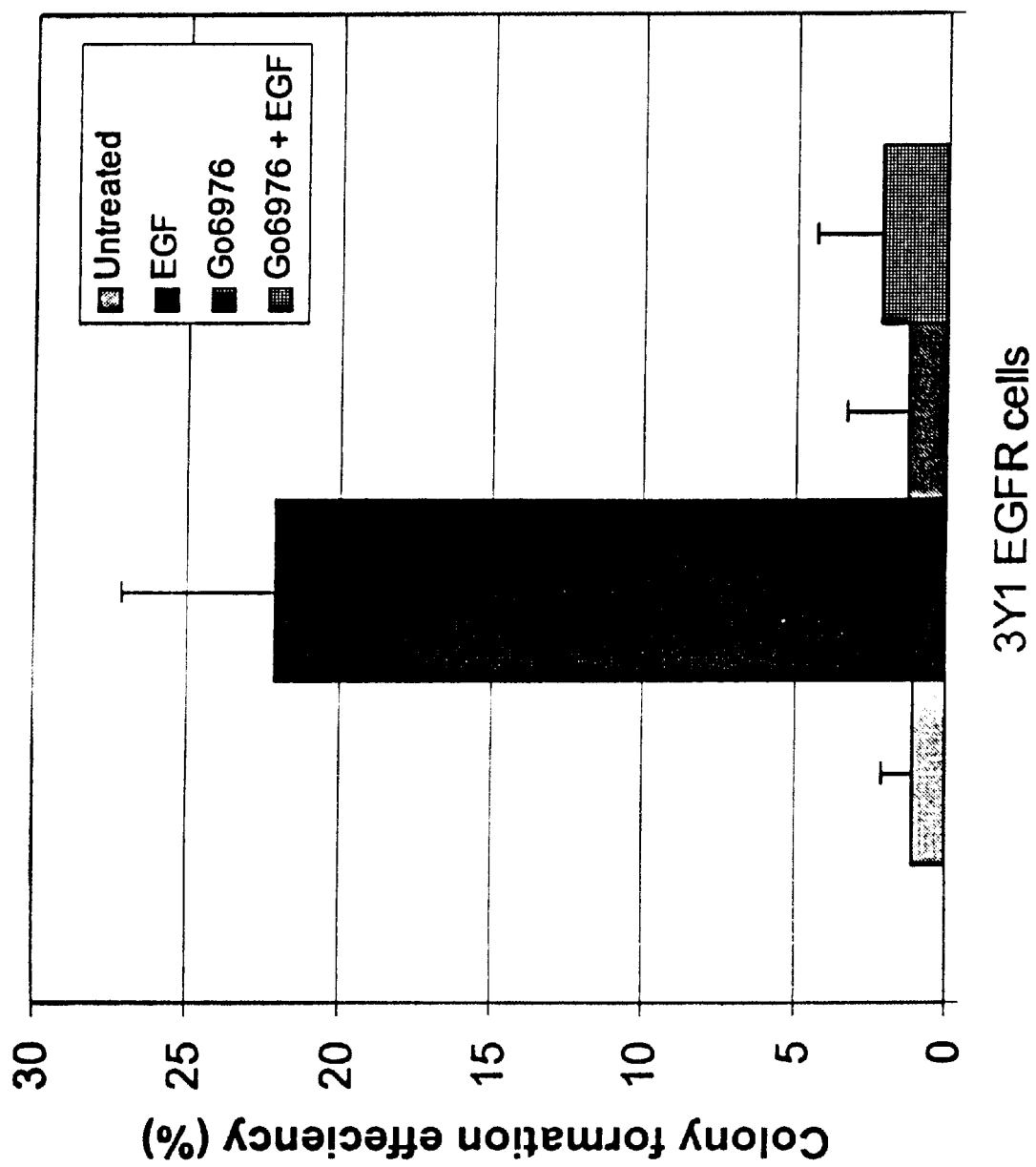

FIG. 8 shows the effect of Gö6976 for blocking cell transformation caused by epidermal growth factor (EGF). 3Y1 cells overexpressing EGF receptors showed a transformed morphology upon 100 ng/ml EGF treatment for 24 hours. Co-treatment with 250 nanamoles Gö6976 and EGF completely blocked EGF-induced cell transformation while treatment with Gö6976 alone did not show any toxic effect on 3Y1 EGFR cells.

The effect of Gö6976 on blocking EGF-induced cell transformation was further confirmed by checking anchorage-independent cell growth. As shown in FIG. 8, cultures of $1 \times 10^3$ 3Y1 cells overexpressing EGF receptors were prepared by suspending the cells in soft agar. One sample was left untreated, one was treated with 100 ng/ml of EGF, one sample was treated with 100 ng/ml of EGF and 250 nanamoles of Gö6976 and one sample was treated with 250 nanaomoles of Gö6976. In each case the percentage of cell forming colonies were determined three weeks after suspending the cells in soft agar. Colony forming efficiency of EGF was greatly reduced by Gö6976.

No Significant Effect on Normal Cells

Applicant tested Gö6976 on normal cells including rat 3Y1 fibroblast in the concentrations used in the above-described experiments and no significant toxic effects on the cells were noted. Toxic effects begin to show up at concentrations of about 5 micromoles in these types of cells.

Second Set of Experiments

Approximately one year following the first set of experiments a second set of experiments was conducted to test Gö6976 on additional cancers and to determine if chemical compounds similar to Gö6976 were effective as a cancer treatment. This second set of experiments are described below:

Cell Culture

Cell cultures of the following cancer cells were used in this second set of experiments. The cell cultures were supplied by the American Type Culture Collection, Rockville, Md.:

DU145 human prostate cancer cells,
A549 human lung cancer cells,
HepG2 human liver cancer cells,
AGS human gastric cancer cells,
T84 human colorectal cancer cells,
C6 glioma cells
Hela human cervical cancer cells
MDA-MB-468 human breast cancer cells These cells were maintained in Dulbecco's modified Eagle medium (DMEM) supplemented with 10 percent bovine calf serum.

Materials

Gö6976 was obtained from Calbiochem and Alexis.

Cell Viability Assay

Cells were seeded for 24 hours. Then they were either treated with Gö6976, C-o 002, or C-o 003, or left untreated. The cells were then collected periodically and evaluated using trypan blue dye exclusion to asses viability using the method described by CY Chen, et al, in J.Biol. Chem. 273:16700–16709.

Experimental Results

Effect of Gö66976 on Prostate, Liver, Gastric and Coloredtal Cancer Cells

Gö66976 treatment led to the apoptosis (programmed cell death) of prostate cancer cell, liver cancer, gastric cancer cells, and colorectal cancer cells.

Results

Two sets of approximately $5 \times 10^5$ DU145 prostate cancer cells, HepG2 liver cancer cells, AGS gastric cancer cells, and T84 colorectal cancers were seeded and 24 hours later one of the sets were treated with 2 μm Gö6976. Seven days after treatment, viable cells were counted. As shown in Table 1, while untreated cancer cells almost double the cell number every 24 hours, the cancer cells treated with Gö6976 were significantly reduced in number, especially DU145 prostate cancer cells, HepG2 liver cancer cells, AGS gastric cancer cells which had no cells survive after treatment while only a very limited number of T84 colorectal cancers cells survived.

TABLE 1

|  | DU145 | AGS | HepG2 | T84 |
|---|---|---|---|---|
| untreated | $7.1 \times 10^7 \pm 0.3 \times 10^7$ | $6.2 \times 10^7 \pm 0.19 \times 10^7$ | $6.0 \times 10^7 \pm 0.27 \times 10^7$ | $1.9 \times 10^7 \pm 0.11 \times 10^7$ |
| treated | 0 | 0 | 0 | $1.1 \times 10^4 \pm 0.11 \times 10^4$ |

Effect of Gö6976 on Brain Tumor Cells and Cervical Cancer Cells

Figure 10:
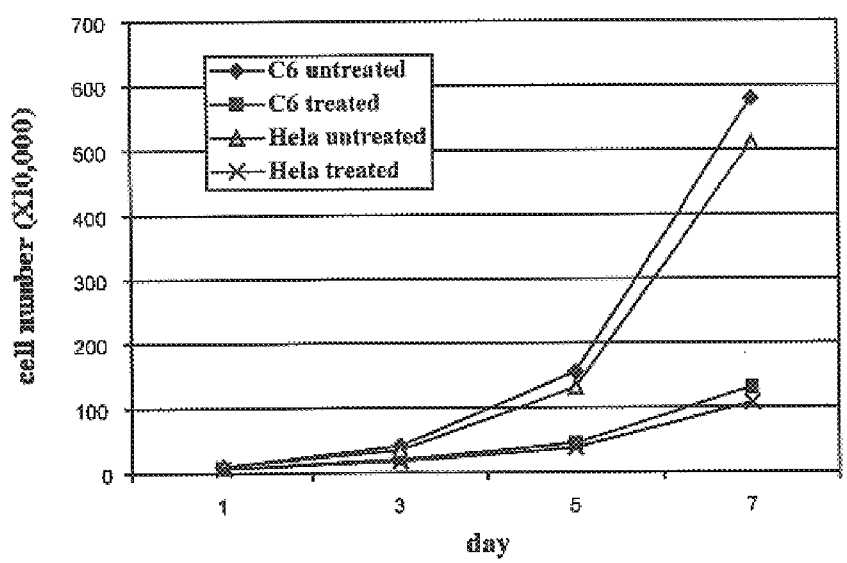
FIG. 10 is a graph showing test results.

Two sets of approximately $5 \times 10^5$ C6 glioma cells and Hela cervical cancer cells were seeded and treated or untreated with 2 μm Gö6976 for 7 days. As shown in FIG. 10, treatment with Gö6976 significant inhibited the growth of C6 glioma cells and Hela cervical cancer cells.

Chemical Compounds Similar to Gö6976

To investigate whether the derivatives of Gö6976 or its structure-related chemical compounds also have the therapeutic effect on cancer, the following two compounds are given for illustrating that the derivatives of Gö6976 have similar effects.

The Synthesis of C-o 002

Figure 9A:
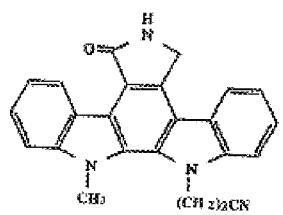
FIGS. 9A, 9B and 9C compare the structure of Gö6976 with other similar chemical compounds.
Figure 9B:
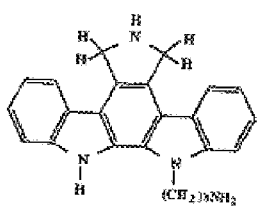

The compound known as C-o 002 is chemically similar to Gö6976 as shown by comparing FIG. 9A which describes Gö6976 and FIG. 9B which describes C-o 002. C-o 002 is also described as follows: 12-(3-Aminopropyl)-5,6,7,12,13-pentahydro-indolo[2,3,-a] pyrrolo [3,4-c] carbazole. This commpound may be prepared in accordance with the following procedure: A quantity of 27 mg (0.71 mM) lithium aluminum hydride was dissolved in 50 ml pure diethyl ether in nitrogen gas on ice. A quantity of 36 mg (0.37 mM) 100% $H_2SO_4$ was added into the above solution and kept at room temperature for 1 hour. The solution made above was then mixed slowly with 35 ml pure diethyl ether, which contains 36.2 mg (0.1 mM) in 12-(2-Cynoethyl)-, 6,7,12,13-tetrahydro-5-oxo-5H-indolo [2,3-a] pyrrolo [3,4-c] carbazole; then refluxed for 30 hours. Ice-cold water was added into reaction for decomposing extra lithium aluminum hydride. The solution was neutralized to a pH over 7 with 10% sodium hydroxide. The organic layer was extracted and the rest organic substance was further extracted with 30 ml diethyl ether for three times. The diethyl ether was evaporated from the combined organic portion. DMSO mixed with diethyl ether was then added and the precipitated product, 12-(3-Aminopropyl)-5,6,7,12,13-pentahydro-indolo [3,4-c] carbazole, was decomposed at the temperature over 293° C.

Synthesis of C-o 003

Figure 9C:
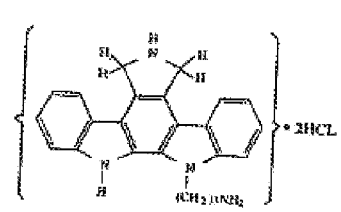

The compound known as C-o 003 is chemically similar to Gö6976 as shown by comparing FIG. 9A which describes Gö6976 and FIG. 9C which describes C-o 003. C-o 003 is described as follows: 12-(3-Aminopropyl)-5,6,7,12,13-pentahydro-indolo[2,3,-a] pyrrolo [3,4-c] carbazole hydrochloride. This compound may be prepared in accordance with the following procedure: A quantity of 35.4 mg (0.1 mM) 12-(3-Aminopropyl)-5,6,7,12,13-pentahydro-indolo [2,3,-a] pyrrolo [3,4-c] carbazole was dissolved in DMSO-diethyl ether solvent. The solution was saturated with HCL gas and distilled under lowered pressure. The final product was precipitated with DMSO-diethyl ether and decomposed at the temperature over 324° C.

Effects of C-o 002 and C-o 003 on Human Cancer Cells

Two sets of approximately $5 \times 10^5$ human MDA-MB-468 breast cancer cells, DU145 human prostate cancer cells, A549 lung cancer cells, AGS gastric cancer cells, and T84 colorectal cancer cells were seeded and treated with 14 μm C-o 002 and C-o 003 24 hours later. Seven days after treatment, viable cells were counted. As shown in Table 2, MDA-MB-468 breast cancer cells, DU145 human prostate cancer cells, HepG2 liver cancer cells and AGS gastric cancer cell after being treated with C-o 002 or C-o 003 go to apoptosis while A549 lung cancer cells and T84 colorectal cancer cells significantly reduced viable cell numbers.

TABLE 2

| | MDA-MB- | DU145 | AGS | HepG2 | A549 | T84 |
|---|---|---|---|---|---|---|
| untreated | $2.1 \times 10^7 \pm 0.13 \times 10^7$ | $5.6 \times 10^7 \pm 0.16 \times 10^7$ | $6.2 \times 10^7 \pm 0.19 \times 10^7$ | $6.6 \times 10^7 \pm 0.24 \times 10^7$ | $5.7 \times 10^7 \pm 0.2 \times 10^7$ | $1.9 \times 10^7 \pm 0.11 \times 10^7$ |
| treated with C-o 002 | 0 | 0 | 0 | 0 | $7 \times 10^5 \pm 0.19 \times 10^3$ | $1.9 \times 10^4 \pm 0.13 \times 10^4$ |
| Treated with C-o 003 | 0 | 0 | 0 | 0 | $8.5 \times 10^5 \pm 0.3 \times 10^3$ | $2.7 \times 10^4 \pm 0.15 \times 10^4$ |

Human and Animal Treatment

The above described test show clearly that Gö6976 and chemical compounds similar to it have a strong apototic effect on a variety of human cancer cells and that it can inhibit growth of other human cancer cells. Based on the EGF experiments showing a blocking of the effects of the EGF induced cell transformation, Gö6976 and similar chemical compounds also can be used as a cancer preventive reagent. The lack of toxic effects on normal cells at the concentrations needed for effectiveness against the cancer cells shows that Gö6976 and similar chemical compounds are very valuable chemotheraputic reagents. It could be applied in many of the well-known methods currently used for chemotheraputic treatment. For example, it may be injected directly into tumors, injected into the blood stream or body cavities or taken orally or applied through the skin with patches. The dose chosen should be sufficient to constitute effective treatment but not so high as to cause unacceptable side effects. The state of the cancer and the health of the patient should preferably be closely monitored during and for a reasonable period after treatment.

While the above examples describe the effectiveness of Gö6976 and similar compounds as chemotheraputic treatment for various cancers they are not intended as a limitation of the invention. The chemical was effective in killing or reducing the growth rate of all cancer cells tested. Therefore, it should be obvious that it would be effective as a treatment to cancer cells not tested that are associated with increased levels of PKC α expression and/or activity such as bladder tumor, nasopharyngeal carcinoma, human renal cell carcinomas, tumor derived from endrocrine glands such as the pituitary gland and the thyroid gland, pancreatic cancer and melanoma. Derivatives of Gö6976 that are effective in inhibiting PKC α should also be effective as a cancer treatment. Also, since Gö6976 and chemical compounds similar to it prevent cell transformation it should also work as a preventative drug, especially for people having a high risk for particular cancers.

I claim:

1. A method of treating a mammal suffering from a cancer comprising the steps of administering to said mammal a chemical targeted to PKC α and monitoring said mammal to determine state of said cancer;

wherein said cancer is a cancer sensitive to said chemical targeted to PKC α, wherein the amount administered is a quantity sufficient to constitute effective treatment, wherein said chemical is chosen from a group consisting of:

A) Gö6976 (trade name): $C_{24}H_{18}N_{40}$ (formula): 12-(2-Cyanoethyl)-6,7,12,13-tetrahydro-13-methyl-5-oxo-5H-indolo [2,3-a] purrolo[3,4-c] carbazole (chemical name), B) C-o 002 (trade name): $C_{23}H_{22}N_4$ (formula): 12-(3-Aminopropyl)-5,6,7,12,13-pentahydro-indolo [2, 3,-a] pyrrolo [3,4-c] carbazole (chemical name), and C) C-o 003 (trade name): $C_{23}H_{24}N_4Cl_2$ (formula): 12-(3-Aminopropyl)-5,6,7,12,13-pentahydro-indolo [2, 3,-a] pyrrolo [3,4-c] carbazole hydrochloride (chemical name) and wherein said cancer is chosen from a group of cancers consisting of: breast cancer, leukemia, lymphoma, lung cancer, bone cancer, prostate cancer gastric cancer, colon cancer, rectal cancer, liver cancer, cervical cancer, renal cancer, bladder cancer, nasopharyngeal cancer, esophagus cancer, pituitary gland tumor; thyroid cancer melanoma and pancreatic cancer.

2. A method as in claim 1 wherein said chemical is C-o 002 (trade name): $C_{23}H_{22}N_4$ (formula): 12-(3-Aminopropyl)-5,6,7,12,13-pentahydro-indolo[2, 3,-a] pyrrolo [3,4-c]carbazole (chemical name).

3. A method as in claim 1 wherein said chemical is C-o 003 (trade name): $C_{23}H_{24}N_4Cl_2$ (formula): 12-(3-Aminopropyl)-5,6,7,12,13-pentahydro-indolo [2,3,-a] pyrrolo[3,4-c]carbazole hydrochloride (chemical name).

4. A method as in claim 1 wherein said mammal is a human.

5. A method as in claim 1 wherein said cancer is breast cancer.

6. A method as in claim 1 wherein said cancer is leukemia.

7. A method as in claim 1 wherein said cancer is lymphoma.

8. A method as in claim 1 wherein said cancer is lung cancer.

9. A method as in claim 1 wherein said cancer is bone cancer.

10. A method as in claim 1 wherein said cancer is skin cancer.

11. A method as in claim 1 wherein said cancer is prostate cancer.

12. A method as in claim 1 wherein said cancer is gastric cancer.

13. A method as in claim 1 wherein said cancer is colon cancer.

14. A method as in claim 1 wherein said cancer is rectal cancer.

15. A method as in claim 1 wherein said cancer is liver cancer.

16. A method as in claim 1 wherein said cancer is cervical cancer.

17. A method as in claim 1 wherein said cancer is renal cancer.

18. A method as in claim 1 wherein said cancer is bladder cancer.

19. A method as in claim 1 wherein said cancer is nasopharyngeal cancer.

20. A method as in claim 1 wherein said cancer is esophagus cancer.

21. A method as in claim 1 wherein said cancer is pituitary gland tumor.

22. A method as in claim 1 wherein said cancer is thyroid cancer.

23. A method as in claim 1 wherein said cancer is melanoma.

24. A method as in claim 1 wherein said cancer is pancreatic cancer.

25. A method as in claim 1 wherein said chemical is administered by injecting it directly into a tumor.

26. A method as in claim 1 wherein said chemical is administered by injecting it into said mammal's blood stream.

27. A method as in claim 1 wherein said chemical is administered orally.

28. A method as in claim 1 wherein said chemical is administered through said mammal's skin.

29. A method as in claim 1 wherein said chemical targeted to PKC α is administered in combination with prior art chemotherapy agents.

30. A method as in claim 1 wherein said chemical targeted to PKC α is administered in combination with radiation therapy.

31. A method of preventing cancer comprising the step of administering a chemical described in claim 1 to persons having a high risk of cancer.

* * * * *